United States Patent
Thomas, III et al.

(10) Patent No.: US 6,896,779 B2
(45) Date of Patent: May 24, 2005

(54) CORROSION SENSOR

(75) Inventors: Elvin D. Thomas, III, Ft. Washington, MD (US); Keith E. Lucas, Upper Marlboro, MD (US); Paul Slebodnick, Springfield, VA (US); Elizabeth A. Hogan, Upper Marlboro, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/857,369

(22) Filed: May 21, 2004

(65) Prior Publication Data

US 2005/0000831 A1 Jan. 6, 2005

Related U.S. Application Data

(63) Continuation of application No. 09/816,148, filed on Mar. 26, 2001, now Pat. No. 6,809,506.

(51) Int. Cl.[7] .......................... G01N 27/26; C23F 13/00
(52) U.S. Cl. ............. 204/404; 204/196.02; 204/196.03; 204/196.06; 204/196.07; 204/196.34; 204/196.37; 205/775.5; 205/776; 205/776.5; 205/777; 205/727; 205/728; 205/730; 205/731; 205/740
(58) Field of Search ........................... 204/404, 196.02, 204/196.03, 196.06, 196.07, 196.34, 196.37; 205/775.5, 776, 776.5, 777, 727, 728, 730, 731, 740

(56) References Cited

U.S. PATENT DOCUMENTS

| 4,087,742 A | * | 5/1978 | Khoo | 205/731 |
| 4,755,267 A | * | 7/1988 | Saunders | 205/726 |
| 6,077,418 A | * | 6/2000 | Iseri et al. | 205/775.5 |

* cited by examiner

Primary Examiner—Bruce F. Bell
(74) Attorney, Agent, or Firm—John J. Karasek; Sally A. Ferrett

(57) ABSTRACT

A system using tank corrosion sensors to provide for an overall assessment and monitoring of the electro-chemical corrosion and coatings condition in ships' tanks, and particularly in ships' seawater or compensated fuel tanks. The system includes reference half-cells mounted along a suspended cable and one instrumented sacrificial anode at the end of the cable to provide optimal sensing capability within a tank structure. The reference half-cells and the sacrificial anode measure a potential and current output, respectively. Together the measurements provide objective information that can be used to predict corrosion damage and coating deterioration occurring throughout the structure of the tank. The system may be used for an overall assessment and monitoring of the electro-chemical corrosion and coatings condition. In a preferred embodiment, the measurements are stored in a datalogger that is optimally contained within an associated instrument housing. If used with other systems in other tanks, the system may be used to monitor the relative tank condition, trend tank condition changes over time, range tank behavior into three categories and provide a direct analysis methodology for making tank maintenance decisions.

18 Claims, 9 Drawing Sheets

CORROSION SENSOR

CROSS REFERENCE TO RELATED APPLICATIONS

This application is a continuation of Ser. No. 09/816,148, filed Mar. 26, 2001 now U.S. Pat. No. 6,809,506.

BACKGROUND OF THE INVENTION

1. Field of the Invention

The present invention relates to an corrosion monitoring system, which is used to provide an overall assessment of the materials degradation and the condition of protective coatings in a tank structure in which the metal is subject to corrosion, and particularly relating to a corrosion sensor for use in tanks which contain or intermittently contain conductive electrolyte.

2. Description of the Related Art

Shipboard tanks make up a significant percentage of below deck space in ships and vessels. These tanks are necessary components for the storage of liquids, for example, ballast seawater, compensated fuel/seawater, and a number of other essential liquids. The size and quantity of these tanks vary considerably for each class of ship. Each tank on a ship has a unique geometry, operational use and a set of corresponding environmental factors in which the metals and coatings are exposed. Seawater tanks, used in many ballasting operations, are subject to high salinity conditions, high humidity, the attachment of biological materials to the surfaces and repeated fill/drain cycling. Fuel tanks may be purely fuel storage or in many cases they are compensated with seawater, to minimize hull buoyancy changes as the fuel is consumed. In these compensated tanks, conditions continually vary between a petroleum-based system to that of seawater immersion. Other tanks, such as sewage (combined holding tank) and potable water, are both exposed to unique environments. Tanks are coated differently depending on usage and may or may not have galvanic anode cathodic protection, although all tanks with seawater influx are generally cathodically protected. In addition to basic usage differences, within each tank corrosion conditions and coatings performance may vary considerably. In seawater ballast tanks, areas in residual water are continually immersed in electrolyte and receive cathodic protection most of the time. The corresponding vertical wall areas and overheads undergo routine cycling during normal use and usually have wet/dry conditions along with high humidity and heat. These tanks also contain a significant percentage of structural components, which are difficult to prepare and coat effectively. Overhead coated surfaces, while often wet from condensation and high humidity, fail by effects of gravity and osmotic pressure directly at the coatings surfaces. While each of these areas are exposed to similar conditions, in general, failures for different surfaces may occur at different rates and by different mechanisms. Those tanks located on the ship exterior may additionally receive solar energy and suffer from highly variable temperature and heat cycling effects.

The maintenance of tanks is more than just re-painting the metal surfaces. Tank inspection and assessment alone requires the need for manual opening, gas freeing, staging (if necessary) and entry of trained personnel. In the U.S. Navy alone, thousands of tanks are inspected each year, with an average cost of eight to fifteen thousand dollars per tank. Each tank is typically inspected at least once every dry dock cycle, or nominally at least every 5 to 7 years depending on service or ship class. Once tanks are identified for refurbishment, U.S. Navy fleet tank maintenance costs soar to over $250 million/year. It is most cost effective to perform maintenance (staging, surface preparation, coatings application, and galvanic anode replacement) on only those tanks which are in the worst condition, especially where funds and time are limited. In order to accurately determine which tanks require maintenance, all tanks should be monitored, assessed and correctly identified for maintenance either continually or beforehand, so that the maintenance that is performed is done only when the condition of the tank preservation warrants repair.

Typically, a tank preservation system uses dielectric coatings (e.g. paint) as the primary corrosion barrier and a cathodic protection system as a secondary measure to minimize coatings degradation and to prevent galvanic corrosion of the tank material.

The cathodic protection system for a tank typically consists of a number of sacrificial anodes, typically made of a strongly electro-negative metal such as a zinc or aluminum alloy. The sacrificial anodes are often referred to as "zincs". The sacrificial anodes are distributed through the tank and mechanically attached to the tank walls. Adequate cathodic protection is so beneficial, that in U.S. Navy ships, for example, the anode type and arrangement are defined by a Navy specification. By design, these sacrificial anodes are more "electro-negative" or "anodic" than the tank metal, commonly steel, thus creating a controlled corrosion cell where the sacrificial anode is consumed preferentially to the tank structure. Because the sacrificial anodes are selected to be more negative than most materials, they will also protect other metal components within the tank (e.g. piping, valves, cables). The protection afforded the tank metal also helps minimize premature coatings failure.

The sacrificial anodes are mechanically attached to the tank walls to prevent them from shifting during ship motions and electrically grounded to the tank walls to allow for the conduction of current from the anode to the tank. For good anode performance, anodes are generally directly mounted to the tank walls/structure. When immersed, the sacrificial anodes corrode to produce ions in the electrolyte (fluid in the tank) and correspondingly supplies electrons (current) through the metallic path to the tank surfaces. Because the sacrificial anodes supply electrons to the tank surfaces, a benign chemical reaction occurs at the tank surfaces using the electrons supplied by the anode, instead of the corrosion reaction which would occur at the tank walls if the sacrificial anodes were not present. Ideally, a sufficient number of sacrificial anodes are distributed throughout a tank, so that all areas and components within the tank are influenced by the sacrificial anodes. More sacrificial anodes may be located at the lower points within a tank with varying fluid levels, such as a ballast tank, or in areas which need more protection (e.g. near Cu—Ni piping which passes through the tank or other non-steel components). Typically, placement of the sacrificial anodes in a seawater ballast tank cathodic protection system is weighted ⅔ towards the bottom surfaces of the tank.

Even when the tank is protected by a good dielectric coating, sacrificial anodes play a significant role. No coating system is perfect, and if a coating is damaged, the exposed bare tank metal will be subjected to the tank fluid, with the exposed area being aggressively attacked and corroded. Even if the damage to the coating is small, corrosion begins, and over time, tends to undercut the intact coating around the damage thus enlarging the area of attack and damage. Coatings damage is a progressive event and a large number of small damage spots can contribute to significant damage.

The installation of cathodic protection helps to prevent continued damage at bare areas and minimizes the coating deterioration and undercutting action.

Several events may happen in a tank during the time between tank maintenance. Over time, the coatings system begins to fail and more bare area is exposed. Mechanical damage plays a role, but the coating itself also adsorbs moisture slowly and moisture eventually reaches the metallic surface where corrosion begins. Imperfect or poor coating application may accelerate the moisture absorption effects or target areas which fail sooner. Whatever the failure mechanism, eventually more and more tank metal area requires cathodic protection. As demand on the sacrificial anodes increase to protect more bare area, the sacrificial anodes are consumed faster, because the sacrificial anodes are required to output increasingly greater amounts of current. Eventually, tank coatings failure occurs when the percentage of damage becomes intolerably high or when the cathodic protection system (sacrificial anodes within the tank) can no longer supply enough current with which to protect the amount of bare area.

Maintenance costs in a tank are extremely costly, because the tank requires staging, grit blasting recoating, and installation of fresh sacrificial anodes, under controlled environmental conditions and all in a very difficult non-uniform geometry. Ships with many tanks cannot repaint all tanks on a routine basis and port engineers, with highly limited resources, must decide which tanks must be recoated and when. Tank inspection is necessary in order to identify whether a tank requires maintenance. Most tank maintenance problems fall into several categories often related to the operational aspects of the ship and are roughly identified as:

a) Corrosion/structural damage.
   b) Osmotic disbondment caused by condensation on overhead surfaces.
   c) Coatings degradation caused by normal deterioration, variable tank levels, wet/dry cycling or depletion of cathodic protection.
   d) Failure related to substandard coatings.

The geometry is often unique for each tank and maintenance procedures are often complicated by many complex structural members and baffles. Working conditions within the tanks are often awkward, difficult, and potentially dangerous.

At present, a "man-in-tank", visual tank assessment must be performed by a trained tank coatings inspector in order to inspect the corrosion damage to the tank walls, deterioration of the coating system, and condition of the sacrificial anodes. This method of inspection is costly, time-consuming, and typically subjective in nature. Typically, visual tank inspections require that each tank be drained prior to inspection, toxic gas-freed (i.e. per OSHA/NAVOSH requirements) and subsequently certified to contain an atmosphere suitable for human entry. For each inspection, an inspector must go into the tank and visually inspect all tank surfaces and sacrificial anodes. The subjective nature of a visual inspection and difficulty in observing many areas of the tanks may result in missed areas, misinterpretation of corrosion damage, or poor assessment of general coatings deterioration.

With the economic trend toward increased time between overhauls and decreased maintenance costs, it is particularly important that tank conditions be monitored carefully, so that tanks with the greatest maintenance requirements are correctly identified. Optimally, an inspection scenario would rate all the tanks, examine the coatings degradation "trends" within the group and target those tanks within the population that are in the worst condition. Ideally, to perform this task and defray the manned inspection costs, a tank corrosion monitoring system would be available to reduce or eliminate the costly and time consuming visual inspections. The tank corrosion monitoring system could be part of a condition based maintenance plan that would monitor the coatings degradations, analyze data from tank sensors, and compare and trend the tank conditions relative to each other. Further, such a fast, inexpensive tank monitoring and inspection system would allow scarce resources to be devoted to actual tank maintenance, rather than to labor intensive visual inspection.

Because opening and preparing a tank for human entry is so expensive and time consuming, it is optimal to minimize manned inspections and best to schedule all tank repair and coating work possible within the period the tank is staged and available. Typically ship maintenance is planned months prior to arrival of the ship, requiring schedulers to either estimate tank maintenance needs based on historic tank data, or on tank inspection reports, if they are available. If tank maintenance is incorrectly scheduled, based upon inaccurate and dated human inspections, unnecessary funds may be expended to refurbish areas that do not have critical need, and other necessary-maintenance, which had been deferred in favor of the tank maintenance, may go undone.

Two major sources of data are available to the corrosion engineer concerning the condition of the tank coatings and the cathodic protection, without the need for extensive instrumentation. First, the electrochemical potential of protected steel can be measured using a standard half-cell, such as a silver/silver chloride (Ag/AgCl) reference cell, as discussed by H. H. Uhlig, "Corrosion Handbook" (1955), the disclosure of which is incorporated by reference. Where steel is protected by a zinc galvanic anode system, any bare steel surfaces and even the coated steel surfaces are polarized in an electro-negative direction forcing the steel surfaces to become cathodic, with respect to the galvanic anode. As long as sufficient anode mass is correctly located within the structure and the cathodic area requiring protection does not exceed the current capacity of the sacrificial anodes, then the surfaces will remain protected, as discussed in J. Morgan, "Corrosion Protection", 1960, the disclosure of which is incorporated by reference. Changes in either of these states can be measured using appropriate reference half-cells installed in the tank. No convenient, long term monitoring system is available using standard half-cells, however.

Second, each galvanic (sacrificial) anode supplies electrical current as its part in protecting the metal (typically steel) structure. Measuring this level of electrical current allows a determination of how active the sacrificial anodes are, and the level of current and can be used with Faraday's law to predict anode weight loss and thus predict anode life, based on the rate of anode deterioration. A special purpose instrumented anode can be designed whereby the current output can be measured and subsequently gauged depending on the cathodic protection requirements of the tank. This special purpose sacrificial anode does not need to replace an existing sacrificial anode within the tank, but may be added to the tank in order to measure the necessary data.

A tank corrosion monitoring system that accurately monitored the coatings degradations and corrosion level which measures the current output from an instrumented sacrificial anode and measures the potential from at least one reference half cell is disclosed herein.

SUMMARY OF THE INVENTION

Accordingly, it is an object of the present invention to provide a tank corrosion sensor system in which a monitoring and overall assessment of the electrochemical corrosion and coatings condition in a liquid storage tank is provided.

Objects of the present invention are achieved by providing an apparatus which include a half-cells measuring a potential of a tank. The measured potential indicates an amount of corrosion of the tank and the level of tank protection provided by the coatings and cathodic protection system.

Objects of the present invention are achieved by providing an apparatus which includes an anode measuring a current output of a tank. The measured current output indicates an amount of corrosion of the tank and the amount of tank coating degradation.

Objects of the present invention are achieved by providing an apparatus which includes half cells measuring a potential which corresponds to a polarization of a tank. The apparatus also includes an anode measuring a current output of the tank. The polarization and the measured current output together indicates an amount of corrosion of the tank and a level of tank protection provided by the coatings and cathodic protection system.

Objects of the present invention are achieved by providing a method which includes measuring a potential which corresponds to a polarization of a tank. The method also includes measuring a current output of the tank. The polarization and the measured current output together indicates an amount of corrosion of the tank and the amount of tank coatings loss.

Objects of the present invention are achieved by providing an apparatus which includes first means for measuring a potential which corresponds to a polarization of a tank. The apparatus also includes a second means for measuring a current output the tank. The polarization and the measured current output together indicates an amount of corrosion to the tank and the amount of tank coatings loss.

Another object is to provide a fast, objective, effective method for easily comparing ship tanks according to which is most in need of maintenance.

Another object is to provide a corrosion monitoring system which is easily integrated into a condition based monitoring program for a ship.

Another object is to provide a method for evaluating the condition of ship tank coatings so tanks requiring maintenance are objectively identified and ranked in order of greatest need.

Additional objects and advantages of the invention will be set forth in part in the description which follows, and, in part, will be obvious from the description, or may be learned by practice of the invention.

BRIEF DESCRIPTION OF THE DRAWINGS

These and other objects and advantages of the invention will become apparent and more readily appreciated from the following description of the preferred embodiments, taken in conjunction with the accompanying drawing of which.

DESCRIPTION OF THE PREFERRED EMBODIMENTS

Figure 1:
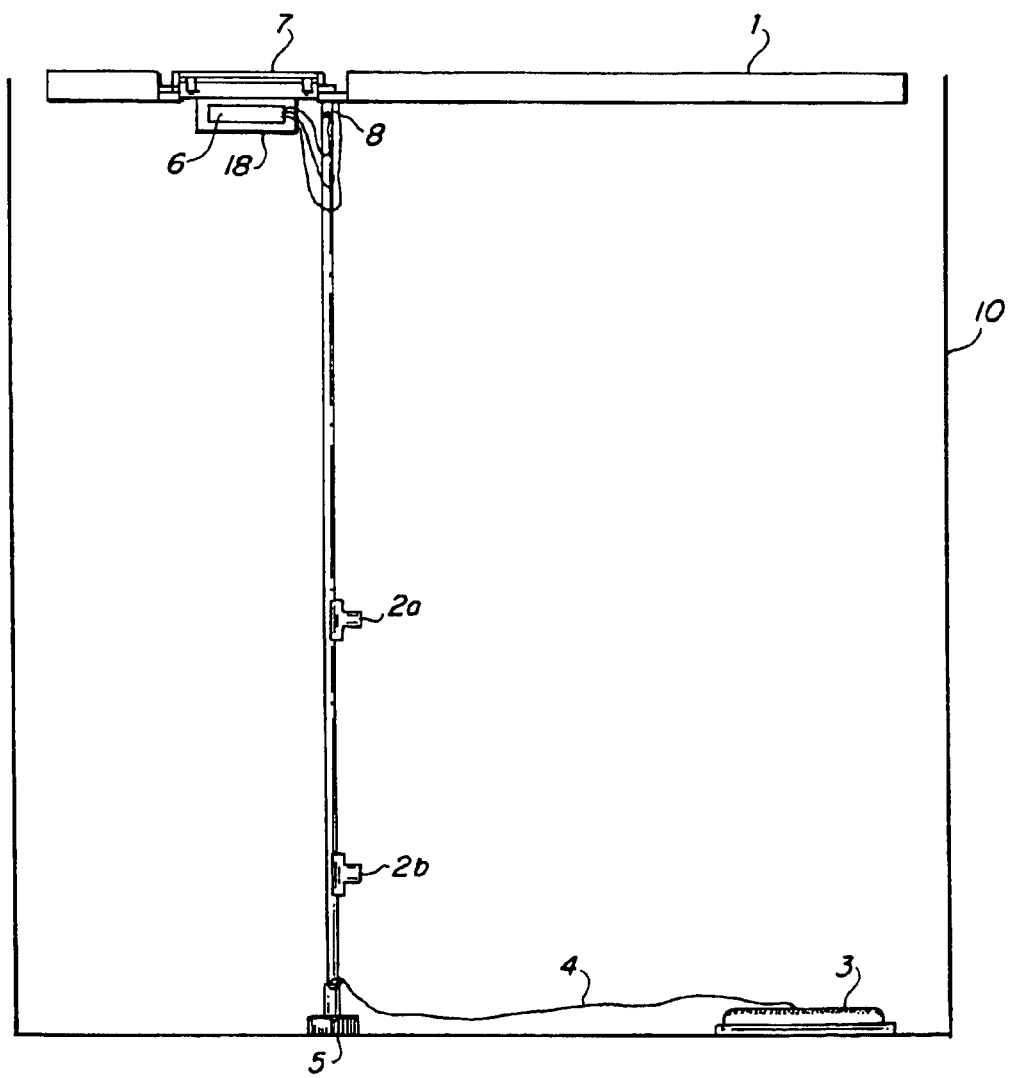
FIG. 1 is a diagram illustrating a tank corrosion monitoring system according to an embodiment of the present invention.

Reference will now be made in detail to the present preferred embodiments of the present invention, examples of which are illustrated in the accompanying drawings, wherein like reference numerals refer to like elements throughout.

FIG. 1 is a diagram illustrating a preferred embodiment of a tank corrosion monitoring system 1 for use within a tank 10, according to a preferred embodiment of the present invention. The corrosion monitoring system 1 is a self contained package intended for in-situ installation within an individual ballast or compensated fuel tank. The corrosion monitoring system 1 includes: two reference half cells 2a and 2b, an instrumented sacrificial anode 3, a cable 4 for suspending the reference half cells 2a and 2b within the tank 10, a magnetic cable tensioner 5, a datalogger 6 for storage of voltage and current data, and a waterproof electronics enclosure 18.

The two potential reference half-cells 2a and 2b, shown in FIG. 1, are Silver/Silver Chloride (Ag/AgCl) seawater reference half-cells (sensors). The half-cells are placed at different levels of the tank, in order to gather data at different tank levels. A half-cell 2a measures the potential $E_{corr}$ of the tank at the location near the half-cell 2a.

The potential across each reference half-cell 2a and 2b is carried in a wire, which is optimally within cable 4. Cable 4 is suspended vertically in the tank 10 and is magnetically attached to the bottom of the tank by a magnetic tensioner 5 to reduce cable 4 movement. The tank magnetic tensioner 5 is a 130 lb pull ceramic magnet, although other attachment means may be used. The length of the cable 4 is selected to correspond with the geometry and size of the tank 10. Optimally, the cable 4 is suited to its environment, being, for example, resistant to corrosion and wear and meeting requirements for fuel tank service or seawater SWU (smoke, waterproof, underwater) specification requirements. The cable 4 includes sufficient wires for carrying electric current from the instrumented sacrificial anode 3 and the potential across each reference half-cell 2a and 2b. In this embodiment, the cable 4 was a four-wire cable, although three wires would have been sufficient.

The instrumented sacrificial anode 3 is also attached to an end of the cable 4. The length of the cable, therefore, takes into consideration the desired location of the instrumented sacrificial anode 3, the distance required for a strain relief loop 8, and the ease of removing a tank hatch 7 to access the datalogger 6.

The datalogger 6, is contained in a waterproof electronics enclosure 18, which is typically mounted on the inside surface of the tank hatch 7. The datalogger 6 records potential measurements of the reference half-cells 2a and 2b and current output of the sacrificial anode 3.

Optionally, the electronics enclosure 18 can include additional instrumentation, such as a tank level indicator (TLI) datalogger (not shown). Alternatively, a separate tank level indicator datalogger may be contained in a separate electronics enclosure.

The reference half-cells 2a and 2b are suspended within tank 10 with the lower reference half-cell 2b residing near the tank bottom and the upper reference half-cell 2a arranged near the middle of the tank to correspond to intermediate and filled states of the tank. Upon filling the tank with seawater, for example, the lower reference half-cell 2b registers a change in a potential almost immediately as the tank 10 fills. Accordingly, the upper reference half-cell 2a begins to read a potential once water reaches it. During the fill episode, the sacrificial anodes within the tank (the tank cathodic protection system) have increasingly more wet tank area to protect and thus respond by providing more current. The effectiveness of the sacrificial anodes in protecting the tank from the electrolyte, as the tank fills and stabilizes, may be estimated by the potential across the reference half-cells 2a and 2b. Increasing the number of reference half-cells will provide more refined data concerning the anode cathodic protection performance and tank condition, although two reference half-cells s supply a significant amount of information. Analysis of the differential potential measured between the reference half-cells 2a and 2b, for example, may provide information about the direction of current flow, the potential distribution within the tank, the general location of surfaces requiring the greatest current demand and, therefore, indirectly, the location of the most significant coatings deterioration.

The placement alone of two half-cells at different heights within the tank would provide tank fill data, as the reference half-cell reads a potential when it contacts the seawater electrolyte. In compensated fuel tanks, the reference half-cells additionally can distinguish between fuel and seawater. Note that although only two reference half-cells are shown in FIG. 1, in other embodiments, more reference half-cells may be used. Between one and six reference half-cells are believed to be sufficient for most Navy ship tanks.

Figure 2:
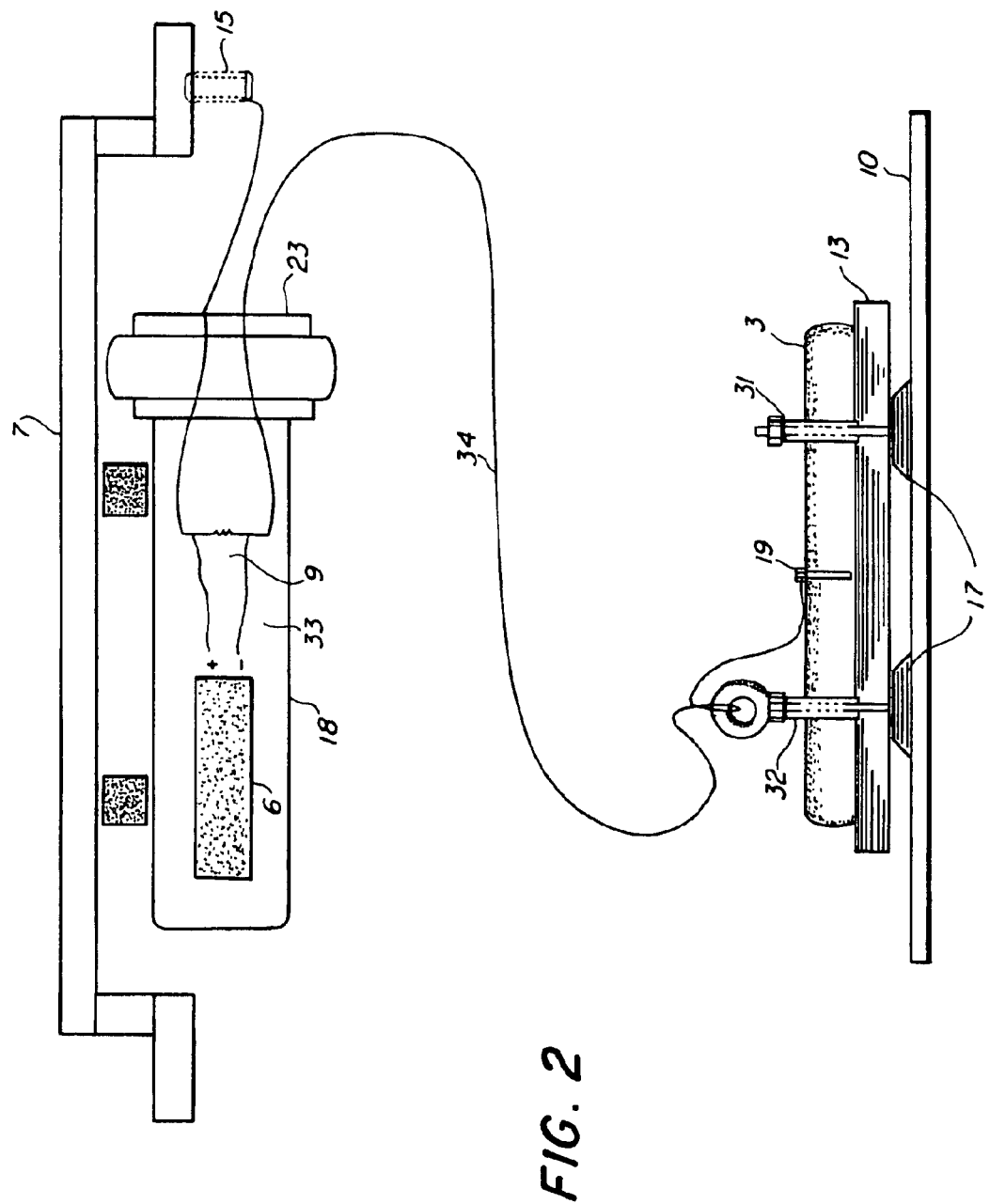
FIG. 2 is a diagram illustrating an instrumented sacrificial anode, according to an embodiment of the present invention.

FIG. 2 is a diagram illustrating an instrumented sacrificial anode, according to an embodiment of the present invention.

In the embodiment shown in FIG. 2, the instrumented sacrificial anode 3 is isolated from the tank 10 metal by a ½" thick PVC plate 13 with length and width dimensions greater than the instrumented sacrificial anode 3 dimensions. The instrumented sacrificial anode 3 is attached to the tank structure 10 by two 110 lb mounting magnets 17, securing bolts 31 and 32. Electrical connection 19 is for electrical attachment between the anode wire 34 and the anode 3. Typically, anode wire 34 is integrated within the cable 4. Note that the ½" PVC plate 13 could have been replaced with some other non-metallic material to electrically isolate the instrumented sacrificial anode 3 from the tank 10.

In order to provide a low resistance ground connection, the anode wire 34 is attached to the sacrificial anode 3 at electrical connection 19. The anode wire 34 is of sufficient gauge to carry the magnitude of current without a voltage drop, typically equivalent to that normally provided by the anode at a direct ground metallic connection. The sacrificial anode wire 34, here contained within cable 4 (shown in FIG. 1), connects through the reference half-cell and connects directly to a shunt resistor 9. The shunt resistor of this embodiment is a low wattage (1–3 Watts), very low resistance (0.1 ohm) resistor and does very little to impede the flow and magnitude of current to ground. Because the shunt resistance is low, the slight voltage drop read across the shunt resistor 9 can be equated directly to the instrumented sacrificial anode current. Electrical leads 33 attached to the ends of the shunt resistor feed into the datalogger 6 and provide both a hull ground reference point and anode current output data, which are stored by the datalogger.

Anode wire 34 within cable 4 enters the waterproof container 18 via a penetration in the watertight bulkhead 23 and correspondingly exits after the shunt resistor 9 in the same manner.

Typically, the instrumented sacrificial anode 3 is selected so that it will behave nearly identically to the actual tank sacrificial anodes, which are distributed in various areas of the tank 10. The instrumented sacrificial anode 3 shown in FIG. 2 is a type ZHC-24 zinc anode, manufactured in accordance with military specification MIL-A-18001J (a commonly used reference specification for sacrificial anodes).

The current output measurement obtained from the instrumented sacrificial anode 3 provides information on the electrical current required to cathodically protect the nearby tank 10 structure. The cathodic current demand of the tank metal, to which both the instrumented sacrificial anode 3 and the tank's sacrificial anodes respond, can be directly correlated to the condition of the tank protective coating system, because poor coatings or high bare area percentages will require more sacrificial anode current to protect. The instrumented sacrificial anode 3 current output may be monitored over time to identify relative changes in the integrity of the tank coatings. During fill episodes of the tank with seawater, the instrumented sacrificial anode 3 responds to the increased surface area under immersion. Typically a tank will require a high current demand immediately after filling until the surfaces equilibrate and establish a stable film. Once stable, the current from the tank's sacrificial anodes drops to what is called a "maintenance current density", which is generally much lower in magnitude and relatively unchanging. Conversely, sacrificial anodes that are unable to sufficiently polarize the structure because of excessive coatings damage, will work at maximum output with very little current drop-off until they are depleted. Information about the current output of a tank's sacrificial anodes can be utilized to aid in assessing coatings damage percentages, damage location, tank condition change over time, anode life prediction and overall anticipated coatings life prediction.

The datalogger 6 typically has multiple channels of analog voltage signal recording and can convert information to digital format for display and plotting. Sufficient analog to digital (A/D) channels are typically included to support the potential measurement from the reference half-cells 2a and 2b and the current output measurement from the instrumented sacrificial anode 3. The DC voltage channels within the datalogger 6 that are used for potential recording typically have minimum resolutions of 0.2 m VDC, and the channels used for instrumented sacrificial anode current output recording typically have minimum resolutions of 0.1 m VDC. Most dataloggers 6 may be set to record at intervals from between 15 times a second to once per day. Typically, however, a datalogger 6 is set to one data reading per hour for each sensor. The datalogger embodiment shown in FIGS. 1 and 2 is battery powered, and preferably has at least 1.5 years of dynamic data storage capacity consistent with the one reading per hour data rate. The unit has a data downloading capability to accomodate easy data retrieval from the hatch or other installed location.

When an optional tank level indicator is used, preferably it will be programmed to collect data at a similar interval (e.g. once every hour), so it may easily be correlated with the current output and potential data.

Optionally, the electronics enclosure may contain only a wire junction box, without a datalogger 6, when the system 1 is electrically wired directly to a ship data storage system outside the tank 10. Alternatively, the wires carrying the voltage and current from the half-cells 2a and 2b and the instrumented sacrificial anode 3 may be routed directly through bulkhead penetrations to an electronics enclosure 18 and datalogger 6 located outside the tank.

Once the system 1 is installed and set to operate, the tank hatch 7 is closed and the tank 10 is sealed for normal operation. To collect data from a hatch mounted 7 configuration, as shown in FIGS. 1 and 2, the hatch 7 is opened and the datalogger 6 accessed by opening the sealed electronics enclosure 18. No manned entry into the tank is required to read a datalogger 6, as the hatch 7 typically can be removed and placed on the deck outside of the tank. In a preferred embodiment, the data is collected from the datalogger 6 via an RS232 serial connection on the electronics enclosure 18.

Once collected, the data may be reduced in standard spreadsheet format and graphed for analysis. The following data are typically collected: (1) time to polarization, (2) current output of the instrumented sacrificial anode, (3) polarization level of the tank, (4) number and levels of tank fill episodes, and (5) reference half-cell differential.

Figure 3:
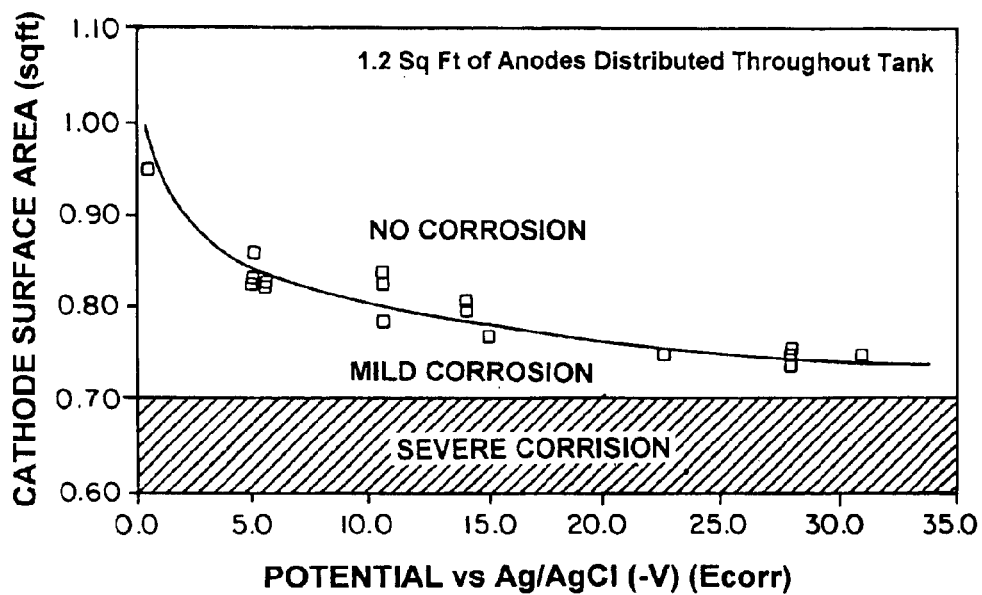
FIG. 3 is a diagram illustrating potential ($E_{corr}$) in negative volts (tank potential referenced to the potential of Ag/AgCl half cell) plotted against the cathodic surface area of a tank.

The measurement of electro-chemical potential provides a significant amount of information concerning the state of overall tank preservation. In FIG. 3, the tank potential ($E_{corr}$) referenced to a Ag/AgCl half-cell is plotted against the cathodic surface area for a steel tank having 1.2 sq ft of sacrificial zinc anodes for cathodic protection. The cathodic surface area is that area of the tank 10 where coatings have deteriorated or where tank metal is exposed to the liquid in the tank. FIG. 3 illustrates how increased cathodic surface area affects the protection potential of the tank. In real terms, the tank contains a finite amount of sacrificial anodes and as the coatings deteriorate the cathodic surface area increases, as indicated. A rise in cathodic surface area results in the decrease in protection levels for a typical sacrificial anode system. More precisely, a tank with little coatings damage would have potentials near −1.0 V, while one with a large coatings damage percentage would have potentials nearer to a freely corroding steel potential of −0.7 V. For a given distribution of sacrificial anodes in a tank, such as the 1.2 square foot, illustrated in FIG. 3, the sacrificial anodes have only a finite amount of current capacity available to protect the coated tank surfaces. As the cathodic area increases, (i.e. a deterioration in coated area) the overall potential of the tank begins to fall off toward more electro-positive potentials. At significant coatings damage percentages, the cathodic protection system (the array of sacrificial anodes) is no longer able to maintain potentials at sufficiently negative levels to effectively protect the tank surfaces, and from that point, coatings deterioration will progress at an accelerated rate. Potential measurements, thus, provide a good indication of tank condition, regardless of the method of coatings failure, because the cathodic protection system will compensate for coatings changes.

If a tank has been recently refurbished (i.e. painted with a good dielectric coating), it will have very little surface area to protect and thus reference half-cells will display potentials at or near the reference levels of the sacrificial anodes. As coatings deteriorate, the rate of polarization during filling of a tank will remain fairly rapid except in two cases. First, there may be such a high percentage of tank coating damage that the sacrificial anodes are no longer able to polarize the structure. Hence, the reference half-cell potentials would begin to drift more electropositive, as indicated in FIG. 3. Second, the sacrificial anodes will gradually be depleted over time to the point that the remaining anode mass has insufficient current capacity to polarize the structure. The use of two or more reference half-cells in the tank, however, provides the ability to track trends in the potential behavior and to compare variations between individual half-cells 2a and 2b. An analysis of differential reference half-cell readings can provide some indication as to coatings damage location, especially where multiple readings or a definite trend has been identified. If damage is uniform throughout the tank, then the reference half-cells will likely read similar potentials and correspondingly have similar rates of polarization. As the damage becomes more localized, the half-cell nearest the failed coatings area will typically shift more electro-positive than the remaining half-cells, thus identifying coatings disparities within the tank.

FIGS. 4–6 will illustrate the use of potential measurement and instrumented sacrificial anode current output to determine the condition of tank coatings and sufficiency of the cathodic protection system. The figures show schematic representations of how tank properties change when a tank is filled with a liquid.

Figure 4A:
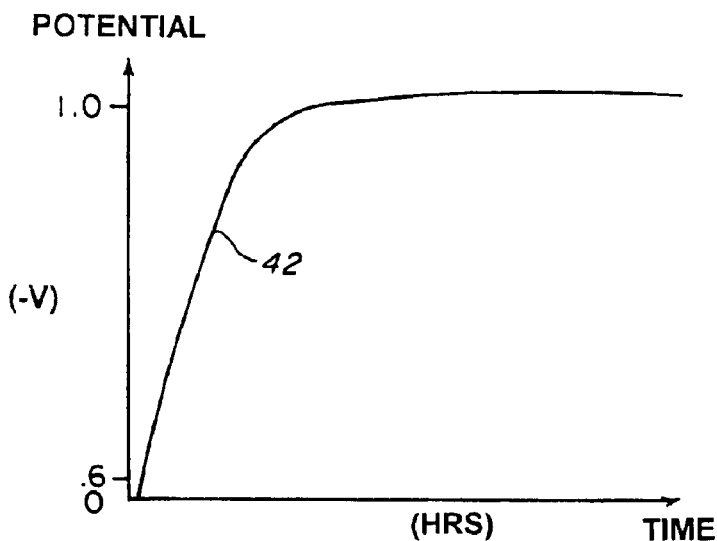
FIG. 4A is a diagram illustrating a tank polarization analysis for a tank in good condition, according to an embodiment of the present invention.
Figure 4B:
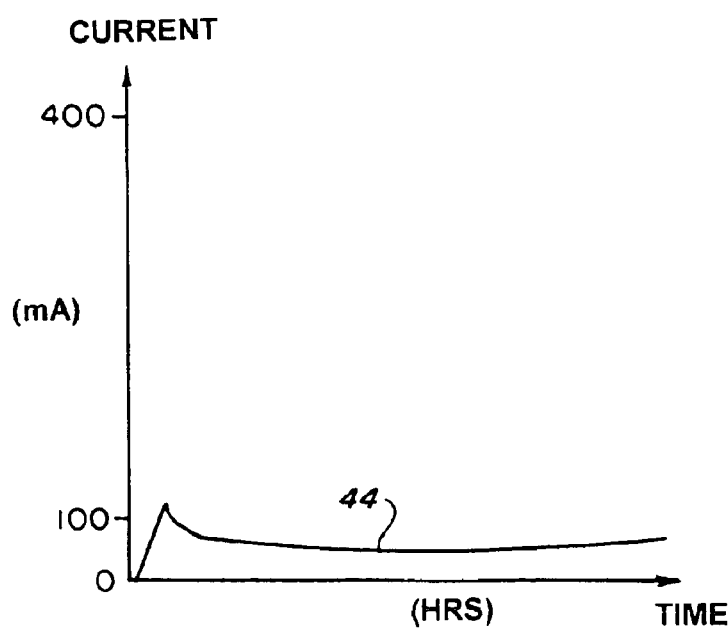
FIG. 4B is a diagram illustrating instrumented sacrificial anode current output analysis for a tank in good condition, according to an embodiment of the present invention.
Figure 5A:
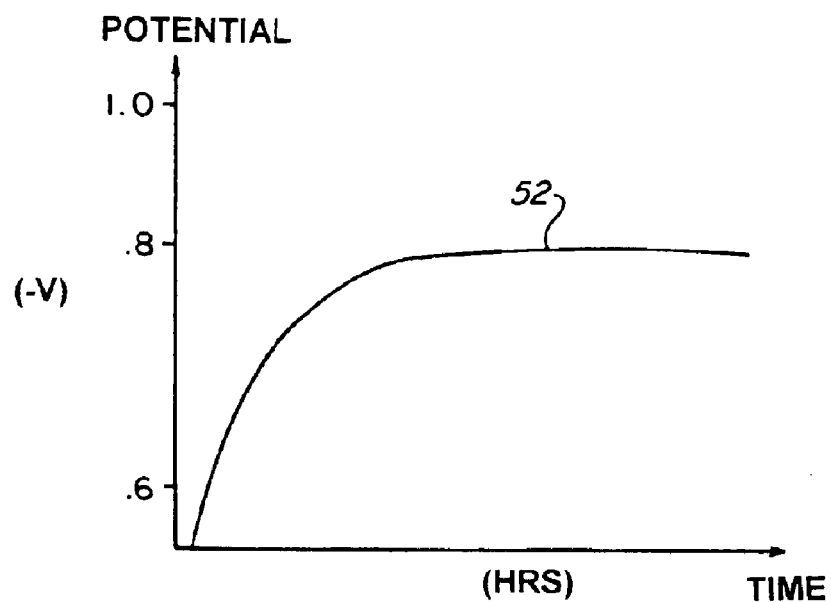
FIG. 5A is a diagram illustrating a tank polarization analysis for a tank beginning to deteriorate, according to an embodiment of the present invention.
Figure 5B:
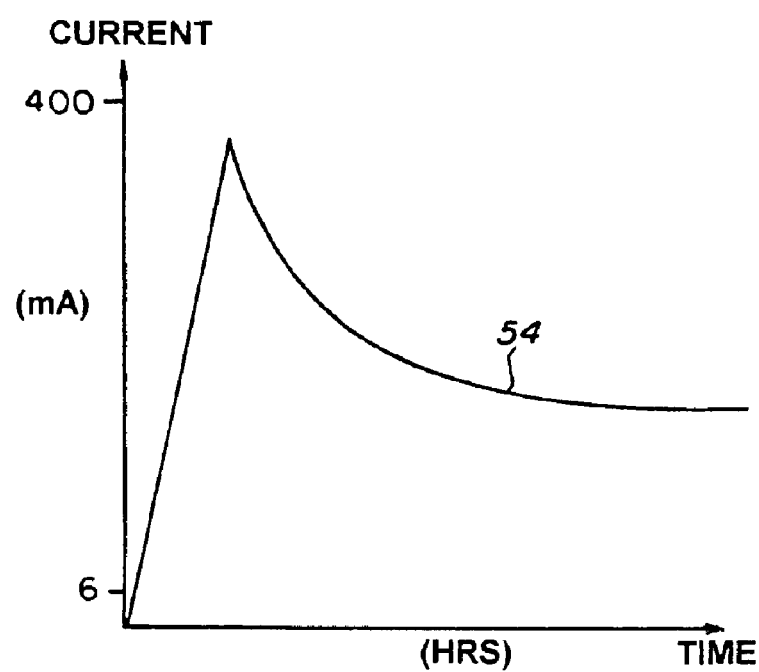
FIG. 5B is a diagram illustrating a instrumented sacrificial anode current output analysis for a tank beginning to deteriorate, according to an embodiment of the present invention.
Figure 6A:
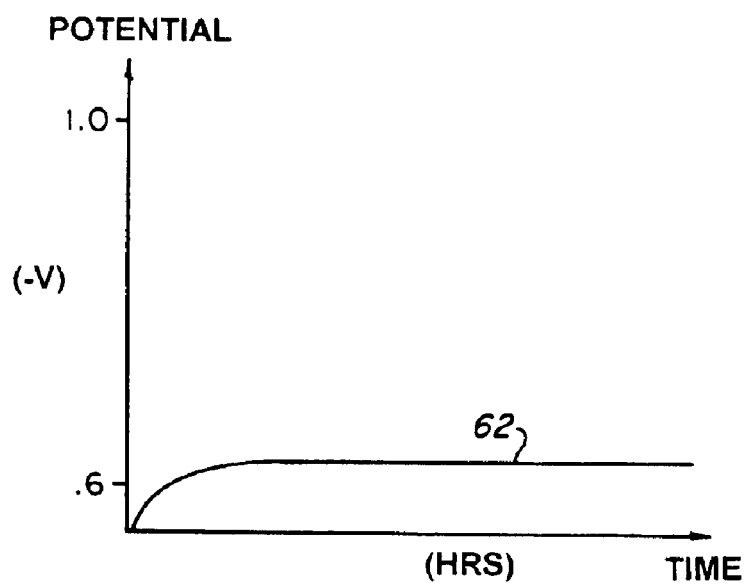
FIG. 6A is a diagram illustrating a tank polarization analysis for a tank in an advanced state of degradation, according to an embodiment of the present invention.
Figure 6B:
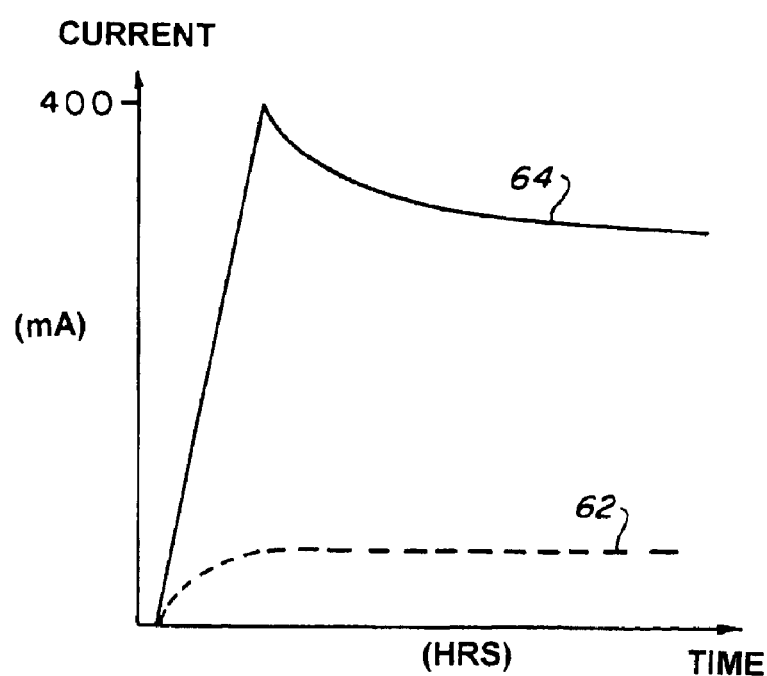
FIG. 6B is a diagram illustrating an instrumented sacrificial anode current output analysis for a tank in an advanced state of degradation, according to an embodiment of the present invention.

FIGS. 4A, 5A, and 6A show a typical polarization scenario of the tank (as measured by a silver/silver chloride half-cell according to the invention) plotted against time, as the tank is filled and remains full. The resultant polarization provides not only the extent of polarization (level of cathodic protection), but also identifies those tanks that polarize immediately verses those which polarize slowly. Given the fixed tank area and an initial state, each filling episode provides a new polarization curve representative of conditions that currently exist and correspondingly provides trend data for long-term prediction. FIGS. 4B, 5B, and 6B show the current output as measured from an instrumented sacrificial anode, corresponding to FIGS. 4A, 5A, and 6A, respectively. At a filling event, the current demand is initially higher and subsequently drops as the surfaces become polarized and less current is required.

FIG. 4A is a diagram illustrating a tank polarization analysis for a newly refurbished tank being filled with a liquid (typically seawater), according to an embodiment of the present invention. Referring now to FIG. 4A, as the tank is filled, the silver/silver chloride potential sensor begins to read when it becomes immersed in seawater, near time zero. Curve 42 portrays the rapid polarization of the tank, from levels near freely corroding steel (−0.6 V), in a negative direction, to values approaching −1.0 V, which is near the maximum zinc anode potential. Potential values more negative than about −0.9 V indicate that minimal or no coating deterioration has occurred, that very little corrosion damage can proceed, and that the tank requires no maintenance.

FIG. 4B is a diagram illustrating the corresponding instrumented sacrificial anode current output data curve 44 for the same recently refurbished tank. Because the tank has been recently refurbished, the current output of the instrumented sacrificial anode is low, since only minimal current is required to polarize the structure. When the tank is filled, the current required by this anode spikes initially, but only to a value less than about ⅓ third of the maximum anode capacity. Immediately, as the tank polarizes, the current begins to drop-off and stabilizes at approximately 75 mA, this stable level referred to as the "maintenance current density". Three factors are of primary importance in an analysis of the curve: the magnitude of maximum current output, the drop off rate, and the maintenance current density level. Each of these values contributes information concerning tank coatings damage percentages, the ability of the cathodic protection system to protect the structure, and projected anode life. Examination of the current output of FIG. 4B and potential measurement of FIG. 4A provide more information than either FIG. 4B or FIG. 4A alone.

FIG. 5A is a diagram illustrating a tank polarization analysis for a tank with a moderate amount of corrosion/coatings damage being filled with liquid (seawater). Referring now to FIG. 5A, the curve 52 is representative of the same layout as that discussed previously. Because the tank has moderate levels of coatings damage, there is a greater percentage of uncoated steel which requires protection. It would, thus, be anticipated that the sacrificial anodes would be required to supply more current, than seen in FIG. 4B, in order to polarize the structure. FIG. 5A reflects this difference in tank condition, because the time to polarization is increased and the level achieved is only approximately −0.8 V. This level of polarization indicates that the tank is adequately cathodically protected, however, it is likely that further coatings deterioration will lead to less protection and subsequently, to greater sacrificial anode material loss. FIG. 5B is a diagram illustrating instrumented sacrificial anode current output analysis for the same steel tank with a moderate amount of corrosion/coatings damage being filled with liquid (seawater). Correspondingly, curve 54 of FIG. 5B shows that the initial anode current required to polarize the structure is high—near the maximum anode output level of −400 mA. In addition, the current drop-off is slower to occur. It can be observed that the "maintenance current density" value of approximately 175 mA is at a greater value than that shown in FIG. 4B, indicating that the cathodic protection system must work harder to protect the tank, and allowing the conclusion that the tank must have some moderate level of coatings damage. It is likely that the remaining sacrificial anodes in the tank are currently adequate to protect the tank. It may be inferred that the sacrificial anodes will be depleted at a faster rate, and that they will require replacement nearer in the future. A reliable quantitative prediction of anode life may be calculated from the current and using Faraday's law.

FIG. 6A is a diagram illustrating a tank polarization analysis for a severely corroded tank being filled with seawater. Referring now to FIG. 6A, the steel tank 10 is in a condition where the cathodic protection system is unable to polarize the structure because there is an excessive amount of coatings damage. The curve 62 does not approach the −1.0 V level, and in fact, shows almost no tank polarization, thus indicating that the steel remains at a freely corroding potential where severe corrosion and continued rapid coatings deterioration is likely. The potential measurement is well below a specific level desired for even minimal cathodic protection. FIG. 6B is a diagram illustrating a instrumented sacrificial anode current output analysis for the same severely corroded tank being filled with seawater, according to an embodiment of the present invention. The instrumented sacrificial anode curve 64 confirms the fact that the tank coatings are in a severely damaged state and that the steel cannot be polarized by the present cathodic protection system. The initial current output, as shown in the first portion of curve 64, rapidly reaches the anode maximum output level of approximately 400 mA and drops off only minimally to approximately 375 mA. This drop-off level is not a "maintenance current density", as evidenced from the inability of the sacrificial anodes to polarize the tank seen in curve 62. It would be presumed that the remaining anode material would be depleted rapidly. Again, a reliable quantitative prediction of anode life may be calculated from the current using Faraday's law.

Another factor that enters into long range prediction is the fact that as a coating ages, the dielectric properties begin to gradually breakdown and even though the coating has not visually or physically failed, the reduced barrier properties also place increasing demand on the cathodic protection system to protect large coated surfaces of the tank 10. As with a coatings failure to bare metal, the current output of the sacrificial anodes ultimately increases until a maximum output level is obtained and the cathodic protection system can no longer maintain the same level of polarization within the tank. This condition, very similar to that shown in FIGS. 6A and 6B, would indicate that the coating system retains little if any barrier capability, that the tank is no longer protected by the coating, and that coating replacement is required immediately.

Figure 7:
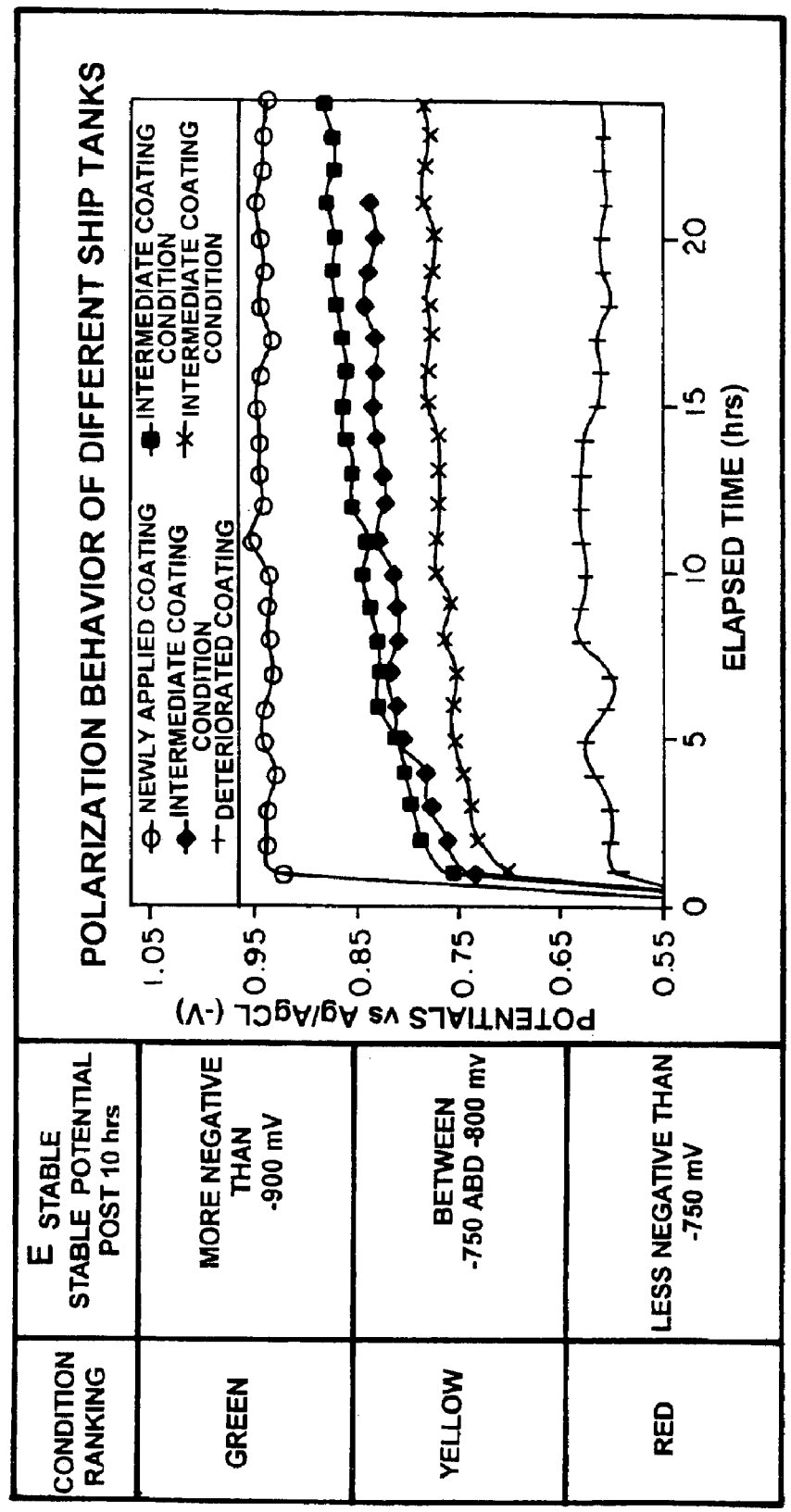
FIG. 7 is a diagram illustrating tank polarization test results for several tanks, according to an embodiment of the present invention.

FIG. 7 illustrates how condition ranking of tanks may be accomplished, and is a diagram illustrating actual test results (tank potential measurements over a period of time) from various test installations on different ship tanks. FIG. 7 shows potential data obtained from the upper reference half-cell acquired from five different ship tanks, using the two reference half-cell configuration. The five curves were taken during a single filling event and clearly discerned different tank states. The potential levels were graded into three condition rankings, which corresponded to a traffic light scenario. "Green" tanks were considered to be trouble free (more electro-negative than about −900 mV) and required no maintenance. Tanks which fell into a "yellow" zone (about −750 mV to about −900 mV) were indicative of increased activity placed on the cathodic protection system and had the requirement for additional current to protect more bare or degrading coatings area. Tanks with nearly freely corroding conditions, fell into the "red" zone (more electro-positive than about −750 mV) and had an unacceptable percentage of corrosion damage. Additionally, the "red" tanks most likely had a failed or significantly overworked cathodic protection system.

Figure 8:
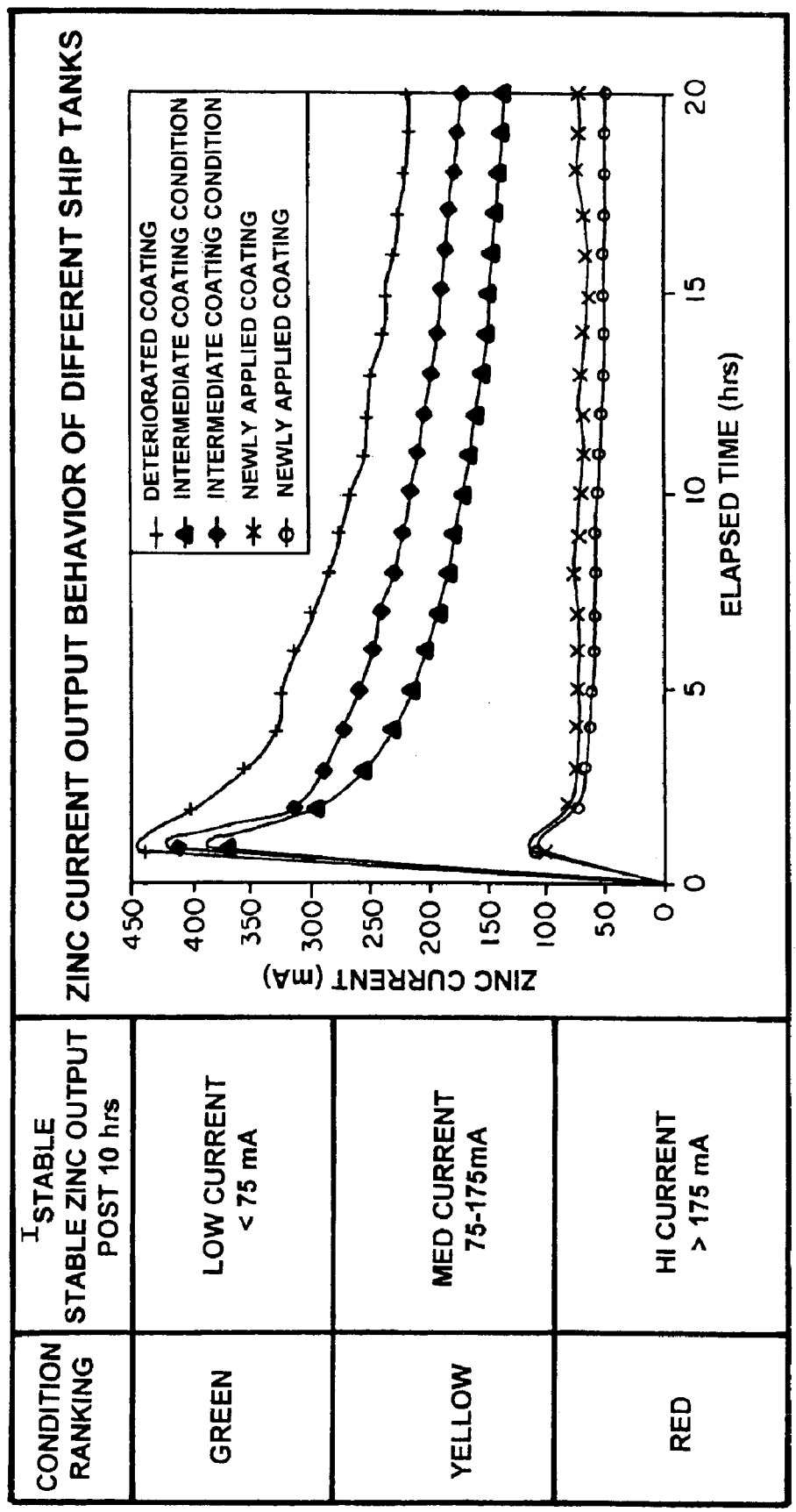
FIG. 8 is a diagram illustrating current output test results for several tanks, according to an embodiment of the present invention.

FIG. 8 is a diagram illustrating actual prototype instrumented sacrificial anode results from test installations aboard various different ship tanks. The "condition ranking" scenario is an aspect of the embodiment of the invention. In FIG. 8, the output current from an instrumented sacrificial anode is plotted verses time in hours and corresponds with potential data shown in FIG. 7. The tanks with newly painted surfaces and low cathodic protection requirements drew a minimal amount of current from the sacrificial anodes. Values for the initial current demand and subsequent drop-off associated with calcareous deposition (stable surface films), were measured and utilized to provide an indicator for long-term requirements on the system. In the tanks where some coatings breakdown had occurred, the sacrificial anodes responded, as expected, and provided an increasing level of current. Once the zinc "maintenance current" output exceeded 75 mA, that tank condition was degraded to the yellow condition state and correspondingly, when the output exceeded 175 mA the condition was changed to a red state.

Figure 9:
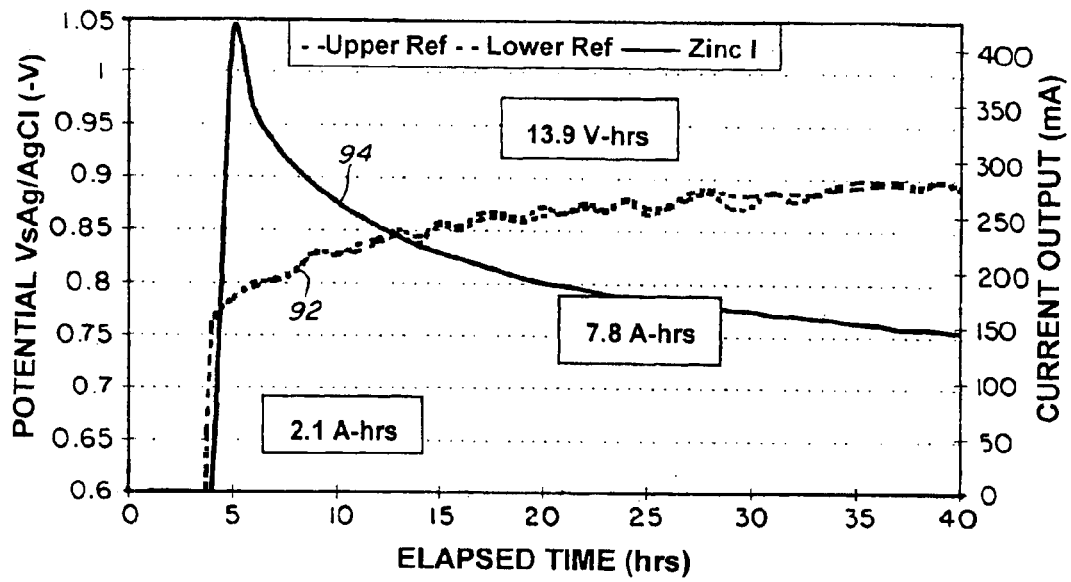
FIG. 9 is a graph of tank polarization test results for tank filling episode in a tank with 9 to 10 year old tank protective coating.
Figure 10:
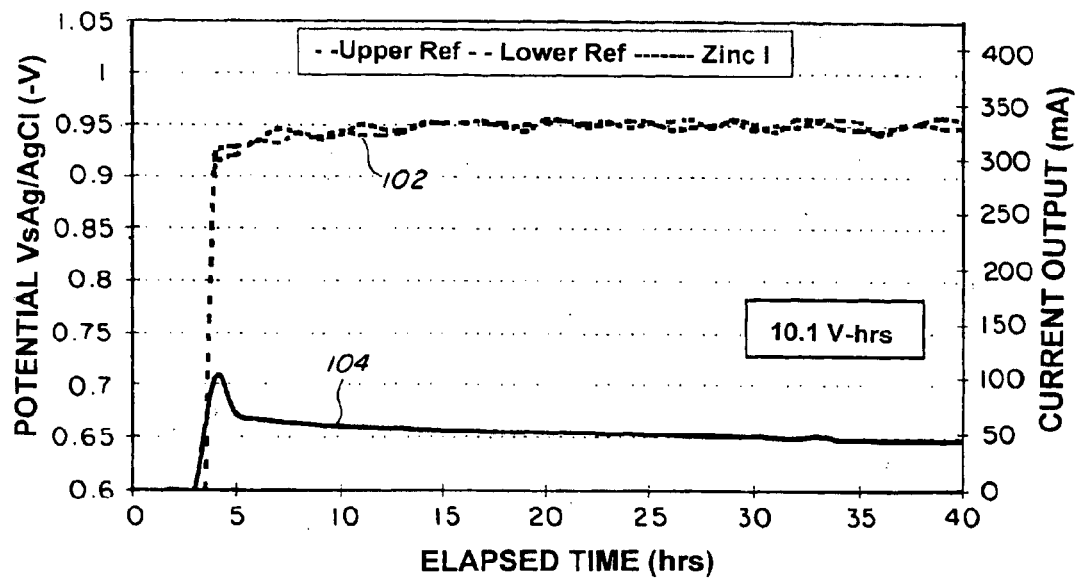
FIG. 10 is a graph of tank polarization test results for tank filling episode in a tank with 1 to 2 year old tank protective coating.

The curves in FIGS. 9 and 10 show an example of a data set for a filling episode in two tanks with widely variable coatings conditions. FIG. 9 shows potential test data 92 taken from reference cells and current data 94 reported from the instrumented sacrificial anode in a tank with a moderate level ("yellow" condition) of damage. FIG. 10, shows test data plotted as potential curve 102 and current curve 104 from an adjacent tank on the same ship, with similar geometry and the same quantity of zinc sacrificial anodes, except that this tank had recently been refurbished and had both a good coatings system and good cathodic protection. The instrumented sacrificial anode and reference half-cells were installed in relatively the same locations in both tanks, with the reference half-cells located 1 m above the bottom and 3 m above, respectively.

FIG. 9 represents data for a 9–10 year old tank coating, while FIG. 10 shows data from a 1–2 year old coating system. In the deteriorating tank condition shown in FIG. 9, the curve 92 indicates that the tank polarized very slowly and did not reach the same level of polarization nor a steady state level of polarization. The corresponding zinc current curve 94 showed an initial spike nearly 4 times that of the newer system of FIG. 1, followed by a gradual decline in current output that mirrored the slow polarization progress of curve 92. The final maintenance current output, of approximately 150 mA, was still 3 times that of the newly coated tank for the same duration, indicating a high current demand, and a moderate level of tank coatings damage.

In FIG. 10, the polarization curve 102 (from the reference half-cells) showed immediate tank polarization along with a corresponding initial spike in the current from the instrumented sacrificial anode 104. With only minimal current necessary to polarize the tank, the current demand curve dropped to a low steady maintenance current of approximately 50 mA, indicating almost no damage to the tank coatings.

In a preferred embodiment of the invention, a reference half-cell is part of a "plug-in" sensor module. The sensor module includes a reference half-cell and connection points which are easily connected to a length of cable. These sensor modules make installation of the system with various numbers of reference half-cells into a tank much easier and faster, and allow quick changeout of reference half cells when necessary.

In an embodiment of the invention, the tank corrosion monitoring system is used in a condition based maintenance method which monitors tank corrosion and coating condition for a number of tanks, ranks the condition of the tanks, and predicts trends. The data provided by the tank monitoring system is used to determine, for example, the status of coatings and cathodic protection systems, the basic location of the coatings damage, the ability of the cathodic protection system to protect the tank, the predicted remaining life of the sacrificial anodes, and the percentage of coatings damage. Data from different tanks is compared and each tank is ranked according to its relative damage and condition. These trend data are used to determine the tank maintenance needs of each ship, without the need for manned entry or periodic visual inspections. This method works with either good-moderate-poor analysis of the tank conditions or with a detailed analysis of each tank. Results are objective in nature and fully documentable. As part of an overall ship husbandry system, this method can significantly lower costs and shorten ship maintenance times.

In another embodiment, instrumented sacrificial anodes and reference half-cells are installed as a part of an integrated ship tank monitoring system. These components also may be integrated into computer systems which monitor the condition of the ship.

One embodiment of the invention is directed to a corrosion sensor system that includes a reference module designed specifically for use in measuring the electrochemical potential of the surface of a tank, a measuring module connected to the reference module for measuring the amount of protection current necessary for condition based monitoring and long term corrosion and coatings assessment, and an electronic module connected to the reference module for monitoring and storing potential and current data to allow for analysis of tank coatings degradation.

In an embodiment, the reference module can include a small hermetically sealed non-metallic enclosure, which contains two cable interconnection connectors, a metallic threaded stud coupling for mounting and a 5-position connector for attachment of the reference sensing element. The reference module can also include a multiple plug-in module array having a single cable interconnection and interconnects variable module quantities and cable lengths for use in measuring the tank electro-chemical potential of a surface of a tank at various heights and with multiple sensor modules, using the two cable interconnection connectors.

The reference module can determine the fill and empty operational cycle of the tank and used to document corresponding tank electrolyte depths concurrent with electrochemical potential measurements. Further, the reference module can evaluate the growth of the calcareous deposits on the metal surface and surface corrosion based on the extent of polarization.

The measuring module can include a sacrificial metal that is electrically isolated from the tank structure using a rigid dielectric barrier and a connector to enable connection to the single interconnection cable. The measuring module can measure, in-situ, an amount of protection current by measuring the voltage drop across a shunt resistor connected to the tank structure, thus providing a direct measurement of actual current necessary to protect the tank. Moreover, the measuring module current measurements can be used to define a protection current requirement, which is supplied by the structure's cathodic protection galvanic anode system. The measuring module data, through direct calculation by Faraday's Law, can predict the condition of permanently installed cathodic protection anodes and the anticipated lifetime before exhaustion.

The electronic module can also include an integral datalogger for data storage at the termination connection of the single interconnect cable. The electronic module can also include a non-metallic enclosure which contains the datalogger, the location for the shunt resistor and connection for the hull grounding cable.

The corrosion sensor system can be utilized in seawater ballast tanks and compensated fuel tanks and, can be utilized to indicate the relative location of coatings damage, tank protection polarization and prediction of galvanic anode system life, regardless of fuel properties.

Another embodiment of the invention is directed to a method for analyzing data acquired from the corrosion sensor system, including storing polarization data from the reference and measuring modules, storing current data from the reference and measuring modules, and combining the polarization and current data from the reference and measuring modules to define a specific range level indicating relative levels of coating damage and tank protection. Combining the polarization and current data can include ranking polarization levels of a tank into levels of (a) less than −900 mV; (b) between −750 and −900 mV; and (c) greater than −750 mV. The current levels in a tank can be ranked into levels of: (a) less than 75 mA; (b) between 75 and 175 mA; and (c) greater than 175 mA.

The method can also include performing trend analysis on said data from which, life-cycle maintenance decisions concerning long-term behavior and changes in the relative location of coatings damage, tank protection polarization, and performing prediction of galvanic anode system life to be monitored and documented in a condition based maintenance approach.

Another embodiment of the invention is directed to a method of installing a corrosion sensor system including attaching metallic studs to the tank wall at desired module locations for support, attaching reference modules to the welded studs of the tank at various heights, attaching measurement modules near the bottom of the tank, attaching a non-metallic enclosure to either the underside of the tank access hatch or outside the tank at an accessible location, and attaching a hull grounding cable to the tank structure or hull of ship or watercraft.

The method of installing the corrosion sensor can also include connecting a desired number of reference modules and measuring module to the single interconnect cable, connecting an interconnect cable to the non-metallic enclosure connector, installing a reference module sensing element into one of five locations provided on the reference cell module connector, as to indicate specific location with respect to other reference modules within the tank, and programming the datalogger to incorporate the number of modules, sampling period and start date.

Although the examples provided herein primarily identify tanks as being tanks within a ship, the invention is not so limited. The systems and methods described herein are equally applicable to other tanks which contain or intermittently contain conductive electrolyte, on other types of vessels, or in stationary applications.

Various numerical values and ranges are described herein, however, the present invention is not limited to such values and ranges. Instead, it should be understood that such values and ranges are only examples of specific embodiments of the invention.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A corrosion sensor system comprising:
   a reference module designed specifically for use in measuring the electrochemical potential of the surface of a tank;
   a measuring module connected to said reference module for measuring the amount of protection current necessary for condition based monitoring and long term corrosion and coatings assessment; and
   an electronic module connected to said reference module for monitoring and storing potential and current data to allow for analysis of tank coatings degradation.

2. The corrosion sensor system of claim 1, whose reference module further comprises:
   a small hermetically sealed non-metallic enclosure, which contains two cable interconnection connectors, a metallic threaded stud coupling for mounting and a 5-position connector for attachment of the reference sensing element.

3. The corrosion sensor system of claim 2, wherein the reference module includes a multiple plug-in module array having a single cable interconnection and interconnects variable module quantities and cable lengths for use in measuring the tank electro-chemical potential of a surface of a tank at various heights and with multiple sensor modules, using the two cable interconnection connectors.

4. The corrosion sensor system of claim 1, whose reference module determines the fill and empty operational cycle of the tank and used to document corresponding tank electrolyte depths concurrent with electro-chemical potential measurements.

5. The corrosion sensor system of claim 1, whose reference module evaluates the growth of the calcareous deposits on the metal surface and surface corrosion based on the extent of polarization.

6. The corrosion sensor system of claim 1, whose measuring module further comprises:
   a sacrificial metal which is electrically isolated from the tank structure using a rigid dielectric barrier and a connector to enable connection to the single interconnection cable.

7. The corrosion sensor system of claim 1, whose measuring module measures, in-situ, an amount of protection current by measuring the voltage drop across a shunt resistor connected to the tank structure, thus providing a direct measurement of actual current necessary to protect the tank.

8. The corrosion sensor system of claim 1, whose measuring module current measurement are used to define a protection current requirement, which is supplied by the structure's cathodic protection galvanic anode system.

9. The corrosion sensor system of claim 1, whose measuring module data, through direct calculation by Faraday's Law, predicts the condition of permanently installed cathodic protection anodes and the anticipated lifetime before exhaustion.

10. The corrosion sensor system of claim 1, whose electronic module further comprises:
    an integral datalogger for data storage at the termination connection of the single interconnect cable.

11. The corrosion sensor system of claim 1, whose electronic module further comprises a non-metallic enclosure which contains the datalogger, the location for the shunt resistor and connection for the hull grounding cable.

12. A corrosion sensor system of claim 1 capable of being utilized in seawater ballast tanks and compensated fuel tanks and, which can be utilized to indicate the relative location of coatings damage, tank protection polarization and prediction of galvanic anode system life, regardless of fuel properties.

13. A method for analyzing data acquired from the corrosion sensor system, comprising:
    storing polarization data from the reference and measuring modules;

storing current data from the reference and measuring modules; and combining said polarization and current data from the reference and measuring modules to define a specific range level indicating relative levels of coating damage and tank protection.

14. A method according to claim 13, wherein said combining further comprises:

ranking polarization levels of a tank into levels of:

less than −900 mV;

between −750 and −900 mV; and greater than −750 mV.

15. The method according to claim 13, wherein said combining further comprises:

ranking current levels of a tank into levels of:

less than 75 mA;

between 75 and 175 mA; and greater than 175 mA.

16. A method according to claim 13, further comprising:

performing trend analysis on said data from which, lifecycle maintenance decisions concerning long-term behavior and changes in the relative location of coatings damage, tank protection polarization, and performing prediction of galvanic anode system life to be monitored and documented in a condition based maintenance approach.

17. A method of installing a corrosion sensor system comprising:

attaching metallic studs to the tank wall at desired module locations for support;

attaching reference modules to the welded studs of the tank at various heights;

attaching measurement modules near the bottom of the tank;

attaching a non-metallic enclosure to either the underside of the tank access hatch or outside the tank at an accessible location; and attaching a hull grounding cable to the tank structure or hull of ship or watercraft.

18. An installation method of the corrosion sensor system reference module and measuring module, according to claim 17, further comprising:

connecting a desired number of reference modules and measuring module to the single interconnect cable;

connecting an interconnect cable to the non-metallic enclosure connector;

installing a reference module "sensing element" into one of five locations provided on the reference cell module connector, as to indicate specific location with respect to other reference modules within the tank; and programming the datalogger to incorporate the number of modules, sampling period and start date.

* * * * *